US006565882B2

(12) United States Patent
Rudnic

(10) Patent No.: US 6,565,882 B2
(45) Date of Patent: May 20, 2003

(54) ANTIBIOTIC COMPOSITION WITH INHIBITOR

(76) Inventor: Edward M. Rudnic, 15103 Gravenstein Way, N. Potomac, MD (US) 20878

(*) Notice: Subject to any disclaimer, the term of this patent is extended or adjusted under 35 U.S.C. 154(b) by 0 days.

(21) Appl. No.: 09/791,536

(22) Filed: Feb. 23, 2001

(65) Prior Publication Data

US 2001/0046984 A1 Nov. 29, 2001

Related U.S. Application Data

(60) Provisional application No. 60/184,582, filed on Feb. 24, 2000.

(51) Int. Cl.⁷ .................. A61K 31/43; A61K 31/545; A61K 9/24; A61K 9/14; A61K 9/16
(52) U.S. Cl. .................. 424/472; 424/464; 424/474; 424/484; 424/489; 424/490; 514/192; 514/200
(58) Field of Search ................ 514/192, 200; 424/464, 474, 484, 489, 490

(56) References Cited

U.S. PATENT DOCUMENTS

| | | | |
|---|---|---|---|
| 4,435,173 A | 3/1984 | Siposs et al. ............... 609/155 |
| 4,616,008 A | 10/1986 | Hirai et al. ................. 514/200 |
| 4,794,001 A | 12/1988 | Mehta et al. ............... 424/458 |
| 4,831,025 A | 5/1989 | Godtfredsen et al. ....... 514/195 |
| 4,904,476 A | 2/1990 | Mehta et al. ............... 424/456 |
| 4,915,953 A | 4/1990 | Jordan et al. ............... 424/473 |
| 4,971,805 A | 11/1990 | Kitanishi et al. ........... 424/494 |
| 5,110,597 A | 5/1992 | Wong et al. ................. 424/438 |
| 5,213,808 A | 5/1993 | Bar-Shalom et al. ....... 424/473 |
| 5,229,131 A | 7/1993 | Amidon et al. |
| 5,395,626 A | 3/1995 | Kotwal et al. ............... 424/472 |
| 5,401,512 A | 3/1995 | Rhodes et al. ............... 424/458 |
| 5,414,014 A | 5/1995 | Schneider et al. .......... 514/535 |
| 5,445,829 A | 8/1995 | Paradissis et al. .......... 424/480 |
| 5,462,747 A | 10/1995 | Radebaugh et al. ........ 424/465 |
| 5,472,708 A | 12/1995 | Chen .......................... 424/451 |
| 5,508,040 A | 4/1996 | Chen .......................... 424/451 |
| 5,567,441 A | 10/1996 | Chen .......................... 424/494 |
| 5,672,359 A | 9/1997 | Digenis et al. ............. 424/463 |
| 5,827,531 A | 10/1998 | Morrison et al. ........... 424/450 |
| 5,840,329 A | 11/1998 | Bai .............................. 424/458 |
| 5,877,243 A | 3/1999 | Sarangapani ................ 524/139 |
| 5,910,322 A | 6/1999 | Rivett et al. |
| 6,027,748 A | 2/2000 | Conte et al. ................ 424/458 |
| 6,132,771 A | 10/2000 | Depui et al. ................ 424/468 |
| 6,294,199 B1 | 9/2001 | Conley et al. .............. 424/468 |
| 6,358,525 B1 | 3/2002 | Guo et al. ................... 424/464 |
| 2001/0046984 A1 | 11/2001 | Rudnic et al. .......... 514/210.09 |
| 2001/0048944 A1 | 12/2001 | Rudnic et al. .............. 424/468 |
| 2002/0004070 A1 | 1/2002 | Rudnic et al. .............. 424/468 |
| 2002/0004499 A1 | 1/2002 | Rudnic et al. .............. 514/192 |

FOREIGN PATENT DOCUMENTS

| WO | WO 94/27557 | 12/1994 |
|---|---|---|
| WO | WO 95/20946 | 8/1995 |
| WO | WO 96/04908 | 2/1996 |
| WO | WO 98/22091 | 5/1998 |

*Primary Examiner*—Thurman K. Page
*Assistant Examiner*—Amy E. Pulliam

(57) ABSTRACT

Antibiotic composition having four dosage forms with different release profiles providing for initial release of a beta lactam antibiotic followed by release of a beta-lactamase inhibitor, followed by release of the antibiotic followed by release of the inhibitor. In a preferred embodiment, release from the second, third and fourth dosage forms is initiated after the component released from the immediately previous form reaches $C_{max}$.

36 Claims, No Drawings

ANTIBIOTIC COMPOSITION WITH INHIBITOR

This application claims the priority of U.S. Provisional Application No. 60/184,582, filed on Feb. 24, 2000.

This invention relates to antibiotics that contain beta-lactam rings that are subject to attack by beta-lactamases in combination with beta-lactamase inhibitors.

Antibiotics with beta-lactam rings, for example, pencillins and cephalosporins, are susceptible to attack from the beta-lactamases (sometimes called penicillinases) that will chemically inactivate the antibiotic. Clavulanic acid, and its derivatives, as well as sulbactam are generally used to bind irreversibly to the beta-lactamase to prevent its activity against such an antibiotic. Typically, there is provided an antibiotic composition that includes the inhibitor with such combinations generally being delivered as an immediate release dosage form.

The present invention relates to an improved antibiotic composition that is comprised of at least four different dosage forms, two of which include at least one antibiotic with a beta-lactam ring (or any portions of such a ring) and two of which include at least one beta-lactamase inhibitor, with the four different dosage forms having release profiles such that there is a first dosage form that releases said at least one antibiotic, a second dosage form that releases at least one beta-lactamase inhibitor, a third dosage form that releases said at least one antibiotic, and a fourth dosage form that releases said at least one inhibitor, with the release profile of the first and second dosage forms being such that the maximum serum concentration of the inhibitor is reached at a time no sooner and preferably after the time at which the maximum serum concentration of the antibiotic released from the first dosage form is achieved, with the third dosage form having a release profile such that the second antibiotic achieves a maximum serum concentration at a time no sooner than and preferably after the time at which the inhibitor released from the second dosage form reaches a maximum serum concentration, and with the fourth dosage form having a release profile such that the maximum serum concentration of the inhibitor released from the fourth dosage form is achieved at a time no sooner and preferably after a time that the maximum serum concentration is reached for the at least one antibiotic released from the third dosage form.

In one preferred embodiment, the initiation of release from the second, third and fourth dosage form occurs at least one hour after initiation of release from the first, second and third form, respectively.

In a preferred embodiment of the present invention, a maximum serum concentration for the antibiotic released from the first dosage form is achieved in no more than about three hours; the maximum serum concentration for the inhibitor released from the second dosage form is reached in a time of from about three to six hours; the maximum serum concentration of the antibiotic released from the third dosage form is reached in from about six to nine hours, and the maximum serum concentration released from the fourth dosage form is achieved in no more than twelve hours, with such times being measured from the time of administration of the antibiotic composition that is comprised of the at least four different dosage forms.

In a preferred embodiment of the present invention, the at least four dosage forms are provided with release profiles such that the inhibitor is released from the second dosage form after the maximum serum concentration is achieved for antibiotic released from the first dosage form; antibiotic is released from the third dosage form after the maximum serum concentration is reached for the inhibitor released from the second dosage form, and inhibitor is released from the fourth dosage form after the maximum serum concentration is reached for the antibiotic released from the third dosage form.

It is to be understood that when it is disclosed herein that a dosage form initiates release after another dosage form, such terminology means that the dosage form is designed and is intended to produce such later initiated release. It is known in the art, however, notwithstanding such design and intent, some "leakage" of antibiotic or inhibitor may occur. Such "leakage" is not "release" as used herein.

Although, in a preferred embodiment there are four dosage forms, it is possible to have more than four dosage forms, provided that there is successive alternate release of antibiotic and inhibitor, and each inhibitor release achieves a serum concentration maximum no sooner than and preferably after the serum concentration maximum of the immediately preceding antibiotic released, and the next antibiotic released reaches a serum concentration maximum no sooner than and preferably after the serum concentration maximum is achieved for the immediately preceding inhibitor dosage form.

In an embodiment of the present invention each of the dosage forms that contains an inhibitor includes such inhibitor in an amount that is effective to inhibit chemical inactivation of the antibiotic by beta-lactamase. In general, the dosage forms that contain the inhibitor contain such an inhibitor in an amount from about 20 percent to about 80 percent.

Similarly, the dosage forms that contain the antibiotic generally include the antibiotic in an amount from about 30 percent to about 80 percent. Each of the dosage forms that deliver antibiotics include from 30% to 70% of the dosage of the antibiotic to be delivered by the composition.

In accordance with a preferred embodiment, the first dosage form that releases antibiotic is an immediate release dosage form. The second, third, and fourth dosage forms are delayed release dosage forms, which may be pH independent or pH dependent (enteric) dosage forms. The second, third and fourth dosage forms are formulated in a matter to provide the release profiles as hereinabove described.

At least four different dosage forms can be formulated into the overall antibiotic composition of the present invention, by procedures generally known in the art. For example, each of the dosage forms may be in the form of a pellet or a particle, with pellet particles being formed into the overall composition, in the form, for example, of the pellet particles in a capsule, or the pellet particles embedded in a tablet or suspended in a liquid suspension.

The antibiotic composition of the prevent invention may be administered, for example, by any of the following routes of administration: sublingual, transmucosal, transdermal, parenteral, and preferably are administered orally. The composition includes a therapeutically effective amount of the antibiotic, which amount will vary with the antibiotic to be used, the disease or infection to be treated, and the number of times that the composition is to be delivered in a day.

The antibiotic product of the present invention, as hereinabove described, may be formulated for administration by a variety of routes of administration. For example, the antibiotic product may be formulated in a way that is suitable for topical administration; administration in the eye or the ear; rectal or vaginal administration; as nose drops; by inhalation; as an injectable; or for oral administration. In a preferred embodiment, the antibiotic product is formulated in a manner such that it is suitable for oral administration.

For example, in formulating the antibiotic product for topical administration, such as by application to the skin, the antibiotic may be formulated for topical administration by including such dosage forms in an oil-in-water emulsion, or a water-in-oil emulsion. In such a formulation, the immediate release dosage forms are in the continuous phase, and the delayed release dosage form is in a discontinuous phase. For example, there may be provided an oil-in-water-in-oil-in-water emulsion, with oil being a continuous phase that contains the immediate release component, water dispersed in the oil containing a first delayed release dosage form, and oil dispersed in the water containing a second delayed release dosage form, and water dispersed in the oil containing a third delayed release dosage form.

It is also within the scope of the invention to provide an antibiotic product in the form of a patch, which includes different antibiotic and inhibitor dosage forms having different release profiles, as hereinabove described.

Furthermore, the antibiotic product with different dosage forms with different release profiles may be formulated for rectal or vaginal administration, as known in the art. This may take the form of a cream or emulsion, or other dissolvable dosage forms similar to those used for topical administration.

As a further embodiment, the antibiotic product may be formulated for use in inhalation therapy by coating the particles and micronizing the particles for inhalation.

In a preferred embodiment, the antibiotic product is formulated in a manner suitable for oral administration. Thus, for example, for oral administration, each of the dosage forms may be used as a pellet or a particle, with a pellet or particle then being formed into a unitary pharmaceutical product, for example, in a capsule, or embedded in a tablet, or suspended in a liquid for oral administration.

Alternatively, in formulating an oral delivery system, each of the dosage forms of the product may be formulated as a tablet, with each of the tablets being put into a capsule to produce a unitary antibiotic product. Thus, for example, antibiotic products may include a first dosage form in the form of a tablet that is an immediate release tablet, and may also include three additional tablets, each of which provides for a delayed release of the antibiotic and inhibitor, as hereinabove described.

As hereinabove described, the antibiotics that are employed in the present invention are ones that include a beta-lactam ring or a portion thereof such as for example, penicillin derivatives, such as penicillin V, penicillin G, penicillin, ampicillin, amoxicillin, carbenicillin, ticarcillin, piperacillin, nafcillin, cloxacillin, dicloxacillin, monobactams such as aztreonam, carbapenems such as imipenem, cephalosporins such as cefoxitan, cephalexin, ceferiaxone, cefuroxime, cefpodoxime, and others.

The beta-lactamase inhibitors maybe any one of a wide variety that are effective to inhibit the action of beta-lactamases on a beta-lactam ring, such as clavulanic acid and its derivatives, sulbactam.

In one embodiment, the product contains sufficient antibiotic for a twenty-four hour period whereby the product is administered once a day.

The Immediate Release Component

The immediate release portion of this system can be a mixture of ingredients that breaks down quickly after administration to release the antibiotic. This can take the form of either a discrete pellet or granule that is mixed in with, or compressed with, the other three components.

The materials to be added to the antibiotics for the immediate release component can be, but are not limited to, microcrystalline cellulose, corn starch, pregelatinized starch, potato starch, rice starch, sodium carboxymethyl starch, hydroxypropylcellulose, hydroxypropylmethylcellulose, hydroxyethylcellulose, ethylcellulose, chitosan, hydroxychitosan, hydroxymethylatedchitosan, cross-linked chitosan, cross-linked hydroxymethyl chitosan, maltodextrin, mannitol, sorbitol, dextrose, maltose, fructose, glucose, levulose, sucrose, polyvinylpyrrolidone (PVP), acrylic acid derivatives (Carbopol, Eudragit, etc.), polyethylene glycols, such a low molecular weight PEGs (PEG2000-10000) and high molecular weight PEGs (Polyox) with molecular weights above 20,000 daltons.

It may be useful to have these materials present in the range of 1.0 to 60% (W/W).

In addition, it may be useful to have other ingredients in this system to aid in the dissolution of the drug, or the breakdown of the component after ingestion or administration. These ingredients can be surfactants, such as sodium lauryl sulfate, sodium monoglycerate, sorbitan monooleate, polyoxyethylene sorbitan monooleate, glyceryl monostearate, glyceryl monooleate, glyceryl monobutyrate, one of the non-ionic surfactants such as the Pluronic line of surfactants, or any other material with surface active properties, or any combination of the above.

These materials may be present in the rate of 0.05–15% (W/W).

The Delayed Release Component

The components in this composition are the same immediate release unit, but with additional polymers integrated into the composition, or as coatings over the pellet or granule.

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit), propylene glycol, and ethylcellulose.

Typically these materials can be present in the range of 0.5–25% (W/W) of this component.

The Enteric Release Component

The components in this composition are the same as the immediate release component, but with additional polymers integrated into the composition, or as coatings over the pellet or granule.

The kind of materials useful for this purpose can be, but are not limited to, cellulose acetate pthalate, Eudragit L, and other pthalate salts of cellulose derivatives.

These materials can be present in concentrations from 4–20% (W/W).

The present invention will be described with respect to the following examples; however, the scope of the invention is not to be limited thereby. Unless otherwise stated, all parts and percentages set forth in this specification are by weight.

Examples
Immediate Release Component

| | Ingredient | Conc. (% W/W) |
|---|---|---|
| Example 1: | Amoxicillin | 65% (W/W) |
| | Microcrystalline cellulose | 20 |
| | Povidone | 10 |
| | Croscarmellose sodium | 5 |

-continued

| | Examples Immediate Release Component | |
|---|---|---|
| | Ingredient | Conc. (% W/W) |
| Example 2: | Amoxicillin | 55% (W/W) |
| | Microcrystalline cellulose | 25 |
| | Povidone | 10 |
| | Croscarmellose sodium | 10 |
| Example 3: | Amoxicillin | 75% (W/W) |
| | Polyethylene glycol 4000 | 10 |
| | Polyethylene glycol 2000 | 10 |
| | Hydroxypropylcellulose | 5 |
| Example 4: | Amoxicillin | 75% (W/W) |
| | Polyethylene glycol 8000 | 20 |
| | Polyvinylpyrrolidone | 5 |
| Example 5: | Clarithromycin | 65% (W/W) |
| | Microcrystalline cellulose | 20 |
| | Hydroxyproplycellulose | 10 |
| | Croscarmellose sodium | 5 |
| Example 6: | Clarithromycin | 75% (W/W) |
| | Microcrystalline cellulose | 15 |
| | Hydroxyproplycellulose | 5 |
| | Croscarmellose sodium | 5 |
| Example 7: | Clarithromycin | 75% (W/W) |
| | Polyethylene glycol 4000 | 10 |
| | Polyethylene glycol 2000 | 10 |
| | Hydroxypropylcellulose | 5 |
| Example 8: | Clarithromycin | 75% (W/W) |
| | Polyethylene glycol 8000 | 20 |
| | Polyvinylpyrrolidone | 5 |
| Example 9: | Ciprofoxacin | 65% (W/W) |
| | Microcrystalline cellulose | 15 |
| | Hydroxypropylcellulose | 5 |
| | Croscarmellose sodium | 5 |
| Example 10: | Ciprofoxacin | 75% (W/W) |
| | Microcrystalline cellulose | 15 |
| | Hydroxypropylcellulose | 5 |
| | Croscarmellose sodium | 5 |
| Delayed Release Component | | |
| Example 11: | Ciprofoxacin | 75% (W/W) |
| | Polyethylene glycol 4000 | 10 |
| | Polyethylene glycol 2000 | 10 |
| | Hydroxypropylcellulose | 5 |
| Example 12: | Ciprofoxacin | 75% (W/W) |
| | Polyethylene glycol 8000 | 20 |
| | Polyvinylpyrrolidone | 5 |
| Example 13: | Ceftibuten | 75% (W/W) |
| | Polyethylene glycol 4000 | 10 |
| | Polyethylene glycol 2000 | 10 |
| | Hydroxypropylcellulose | 5 |
| Example 14: | Ceftibuten | 75% (W/W) |
| | Polyethylene glycol 4000 | 20 |
| | Polyvinylpyrrolidone | 5 |
| Example 15: | Amoxicillin | 65% (W/W) |
| | Microcrystalline cellulose | 20 |
| | Cellulose Acetate Pthalate | 15 |
| Example 16: | Amoxicillin | 55% (W/W) |
| | Microcrystalline cellulose | 25 |
| | Cellulose Acetate Pthalate | 10 |
| | Hydroxyproplmethylcellulose | 10 |
| Example 17: | Amoxicillin | 65% (W/W) |
| | Polyox | 20 |
| | Hydroxypropylcellulose pthalate | 10 |
| | Eudragit E30D | 5 |
| Example 18: | Amoxicillin | 40% (W/W) |
| | Microcrystalline Cellulose | 40 |
| | Cellulose Acetate Pthalate | 10 |
| Example 19: | Clarithromycin | 70% (W/W) |
| | Hydroxypropylcellulose pthalate | 15 |
| | Croscarmellose sodium | 10 |
| Example 20: | Clarithromycin | 75% (W/W) |
| | Polyethylene glycol 2000 | 10 |
| | Eudragit E 30D | 15 |
| Example 21: | Clarithromycin | 40% (W/W) |
| | Lactose | 50 |
| | Eudgragit E 30D | 10 |

-continued

| | Examples Immediate Release Component | |
|---|---|---|
| | Ingredient | Conc. (% W/W) |
| Example 22: | Ciprofoxacin | 65% (W/W) |
| | Microcrystalline Cellulose | 20 |
| | Eudragit E 30D | 10 |
| Example 23 | Ciprofoxacin | 75% (W/W) |
| | Microcrystalline Cellulose | 15 |
| | Hydroxypropylcellulose pthalate | 10 |
| Example 24 | Ciprofoxacin | 80% (W/W) |
| | Lactose | 10 |
| | Eudgragit E 30D | 10 |
| Example 25 | Ciprofoxacin | 70% (W/W) |
| | Polyethylene glycol 4000 | 20 |
| | Cellulose acetate pthalate | 10 |
| Example 26 | Ceftibuten | 60% (W/W) |
| | Polyethylene Glycol 2000 | 10 |
| | Lactose | 20 |
| | Eudgragit E 30D | 10 |
| Example 27 | Ceftibuten | 70% (W/W) |
| | Microcrystalline Cellulose | 20 |
| | Cellulose acetate pthalate | 10 |
| Example 28: | Clavulanate potassium | 65% (W/W) |
| | Microcyrstalline cellulose | 20 |
| | Cellulose Acetate Pthalate | 15 |
| Example 29: | Clavulanate potassium | 55% (W/W) |
| | Microcrystalline cellulose | 25 |
| | Cellulose Acetate Pthalate | 10 |
| | Hydroxypropylmethlycellulose | 10 |
| Example 30: | Clavulanate potassium | 65% (W/W) |
| | Polyox | 20 |
| | Hydroxypropylcellulose pthalate | 10 |
| | Eudragit E 30D | 5 |
| Example 31 | Clavulanate potassium | 40% (W/W) |
| | Microcrystalline cellulose | 40 |
| | Cellulose Acetate Pthalate | 10 |
| Example 32: | Clavulanate potassium | 70% (W/W) |
| | Hydroxypropylcellulose pthalate | 15 |
| | Croscarmellose sodium | 10 |
| Example 33: | Clavulanate potassium | 75% (W/W) |
| | Polyethylene glycol 2000 | 10 |
| | Eudragit E 30D | 15 |
| Example 34: | Clavulanate potassium | 40% (W/W) |
| | Lactose | 50 |
| | Eudragit E 30D | 10 |
| Example 35: | Clavulanate potassium | 65% (W/W) |
| | Microcrystalline Cellulose | 20 |
| | Eudragit E 30D | 10 |
| Example 36: | Sulbactam | 75% (W/W) |
| | Microcrystalline cellulose | 15 |
| | Hydroxyropylcellulose pthalate | 10 |
| Example 37: | Sulbactam | 80% (W/W) |
| | Lactose | 10 |
| | Eudgragit E 30D | 10 |
| Example 38: | Sulbactam | 70% (W/W) |
| | Polyethylene glycol 4000 | 20 |
| | Cellulose acetate pthalate | 10 |
| Example 39: | Sulbactam | 60% (W/W) |
| | Polyethylene glycol 2000 | 10 |
| | Lactose | 20 |
| | Eudragit E 30D | 10 |
| Example 40: | Sulbactam | 70% (W/W) |
| | Microcrystalline cellulose | 20 |
| | Cellulose Acetate pthalate | 10 |
| Example 41: | Clavulanate potassium | 65% (W/W) |
| | Microcrystalline cellulose | 20 |
| | Polyox | 10 |
| | Croscarmellose Sodium | 5 |
| Example 42: | Clavulanate potassium | 55% (W/W) |
| | Microcrystalline cellulose | 25 |
| | Polyox | 10 |
| | Glyceryl monooleate | 10 |
| Example 43: | Clavulanate potassium | 65% (W/W) |
| | Polyox | 20 |
| | Hydroxyproplcellulose | 10 |
| | Croscarmellose sodium | 5 |

-continued

| | Examples Immediate Release Component | |
|---|---|---|
| | Ingredient | Conc. (% W/W) |
| Example 44: | Clavulanate potassium | 70% (W/W) |
| | Polyox | 20 |
| | Hydroxypropycellulose | 5 |
| | Croscarmellose sodium | 5 |

EXAMPLE 45

1 Beta Lactam Antibiotic and Beta-Lactamase Inhibitor Matrix Pellet Formulation and Preparation Procedure 45.1 Pellet Formulation The composition of the antibiotic or inhibitor matrix pellets provided in Table 1.

TABLE 1

| Composition of Antibiotic Pellets | |
|---|---|
| Component | Percentage (%) |
| Antibiotic or Inhibitor | 50 |
| Avicel PH 101 | 20 |
| Lactose | 20 |
| PVP K29/32* | 10 |
| Purified Water | |
| Total | 100 |

*PVP K29/32 was added as a 20% w/w aqueous solution during wet massing.

45.2 Preparation Procedure for Antibiotic or Inhibitor Matrix Pellets 45.2.1 Blend antibiotic or inhibitor and Avicel® PH 101 using a Robot Coupe high shear granulator.

45.2.2 Add 20% Povidone K29/32 binder solution slowly into the powder blend under continuous mixing.

45.2.3 Extrude the wet mass using an LCI Bench Top Granulator. The diameter of the screen of the Bench Top Granulator was 1.0 mm.

45.2.4 Spheronize the extrudate using a Model SPH20 Caleva Spheronizer.

45.2.5 Dry the spheronized pellets at 50° C. overnight.

45.2.6 Pellets between 16 and 30 Mesh were collected for further processing.

45.2.7 The above procedure is used to prepare pellets that contain an antibiotic and pellets that contain an inhibitor.

45.3 Preparation of an Eudragit® L 30 D-55 Aqueous Coating Dispersion 45.3.1 Dispersion Formulation The composition of the aqueous Eudragit L30D-55 dispersion applied to the antibiotic matrix pellets and to the inhibitor matrix pellets is provided below in Table 2.

TABLE 2

| Eudragit ® L 30 D-55 Aqueous Coating Dispersion | |
|---|---|
| Component | Percentage (%) |
| Eudragit ® L 30 D-55 | 55.0 |
| Triethyl Citrate | 1.6 |
| Talc | 8.0 |
| Purified Water | 37.4 |

TABLE 2-continued

| Eudragit ® L 30 D-55 Aqueous Coating Dispersion | |
|---|---|
| Component | Percentage (%) |
| Solids Content | 25.5 |
| Polymer Content | 15.9 |

45.4 Preparation Procedure for an Eudragit® L 30 D-55 Aqueous Dispersion 45.4.1 Suspend triethyl citrate and talc in deionized water.

45.4.2 The TEC/talc suspension is then homogenized using a PowerGen 700 high shear mixer.

45.4.3 Add the TEC/talc suspension slowly to the Eudragit® L 30 D-55 latex dispersion while stirring.

45.4.4 Allow the coating dispersion to stir for one hour prior to application onto the antibiotic matrix pellets.

45.5 Preparation of an Eudragit® S 100 Aqueous Coating Dispersion 45.5.1 Dispersion Formulation The composition of the aqueous Eudragit® S 100 dispersion applied to the inhibitor matrix pellets is provided below in Table 3.

TABLE 3

| Eudragit ® S 100 Aqueous Coating Dispersion | |
|---|---|
| Component | Percentage (%) |
| Part A | |
| Eudragit ® S 100 | 12.0 |
| 1 N Ammonium Hydroxide | 6.1 |
| Triethyl Citrate | 6.0 |
| Purified Water | 65.9 |
| Part B | |
| Talc | 2.0 |
| Purified Water | 8.0 |
| Solid Content | 20.0 |
| Polymer Content | 12.0 |

45.6 Preparation Procedure for an Eudragit® S 100 Aqueous Dispersion Part A:

45.6.1 Dispense Eudragit® S 100 powder in deionized water with stirring.

45.6.2 Add ammonium hydroxide solution drop-wise into the dispersion with stirring.

45.6.3 Allow the partially neutralized dispersion to stir for 60 minutes.

45.6.4 Add triethyl citrate drop-wise into the dispersion with stirring. Stir for about 2 hours prior to the addition of Part B.

Part B:

45.6.5 Disperse talc in the required amount of water 45.6.6 Homogenize the dispersion using a PowerGen 700D high shear mixer.

45.6.7 Part B is then added slowly to the polymer dispersion in Part A with a mild stirring.

45.7 Coating Conditions for the Application of Aqueous Coating Dispersions

The following coating parameters are used for coating with each of the Eudragit® L 30 D-55 and Eudragit® S 100 aqueous film coatings.

| Coating Equipment | STREA 1 ™ Table Top |
| Coater | Laboratory Fluid Bed |
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2 gram per minute |

45.7.1 Coat matrix pellets with L30 D-55 dispersion such that you apply 12% coat weight gain to the pellets.
45.7.2 Coat matrix pellets with L30 D-55 dispersion such that you apply 30% coat weight gain to the pellets.
45.7.3 Coat matrix pellets with S100 dispersion such that you apply 20% coat weight gain to the pellets.
45.8 Encapsulation of the Antibiotic and Inhibitor Pellets Pellets are filled into size 00 hard gelatin capsules at a ratio of 20%: 30%: 20%: 30% Immediate-release matrix pellets (uncoated), L30 D-55 coated pellets 12% weight gain, L30D-55 coated pellets 30% weight gain and S100 coated pellets respectively. The capsule is filled with the four different pellets to achieve the desired dosage.

The immediate release pellets contain the antibiotic; the L30 D-55 12% weight gain coated pellets contain the inhibitor; the L30 D-55 30% weight gain coated pellets contain the antibiotic and the S100 coated pellets contain the inhibitor.

The present invention is advantageous in that the beta-lactamase inhibitor will be dosed at a lower peak concentration, giving rise to fewer side effects. The alternative dosing of the antibiotic and the inhibitor will alternate the exposure to the bacteria in such a way as to make the antibiotic more effective than if they were co-administered, and thereby competing with each other for sites on the bacterial cell wall receptors.

Numerous modifications and variations of the present invention are possible in light of the above teachings, therefore, within the scope of the appended claims, the invention may be practiced otherwise than as particularly described.

What is claimed is:

1. An antibiotic composition comprising:
a mixture of at least four dosage forms, said first dosage form comprising at least one antibiotic with a beta-lactam ring or portion thereof and a pharmaceutically acceptable carrier; the second dosage form comprising at least one beta-lactamase inhibitor and a pharmaceutical carrier; the third dosage form comprising at least one antibiotic including a beta-lactam ring or portion thereof, and a pharmaceutically acceptable carrier; the fourth dosage form comprising at least one beta-lactamase inhibitor and a pharmaceutical carrier, said first dosage form and said second dosage form having release profiles whereby the maximum serum concentration of the inhibitor released from the second dosage form is reached at a time after the maximum serum concentration is reached for the antibiotic released from the first dosage form, the third dosage form having a release profile such that maximum serum concentration of the antibiotic released from the third dosage form is reached at a time after the time at which the maximum serum concentration for the inhibitor released from the second dosage form is achieved, and the fourth dosage form having a release profile whereby the inhibitor released from the fourth dosage form achieves a maximum serum concentration at a time that is after the time at which the maximum serum concentration of the antibiotic released from the third dosage form is achieved.

2. The antibiotic composition of claim 1 wherein the second dosage form initiates release of inhibitor at least one hour after initiation of release of antibiotic from the first dosage form, the third dosage form initiates release of antibiotic at least one hour after initiation of release of inhibitor from the second dosage form and the fourth dosage form initiates release of inhibitor at least one hour after initiation of release of antibiotic from the third dosage form.

3. The antibiotic composition of claim 1 wherein the first dosage form is an immediate release dosage form.

4. The antibiotic composition of claim 1 wherein the inhibitor is released from the second dosage form after the antibiotic released from the first dosage form reaches maximum serum concentration, the antibiotic is released from the third dosage form after the inhibitor released from the second dosage form reaches maximum serum concentration and inhibitor is released from the fourth dosage form after antibiotic released from the third dosage form reaches maximum serum concentration.

5. The antibiotic composition of claim 1 wherein the composition includes the dosage of antibiotic for a twenty-four hour period.

6. The antibiotic composition of claim 1 wherein the antibiotic composition is an oral dosage form.

7. The antibiotic composition of claim 1 wherein the first dosage form includes from 30% to 80% of the antibiotic delivered by the composition and the remainder of the antibiotic is delivered by the third dosage form.

8. The antibiotic composition of claim 4 wherein the first dosage form is an immediate release dosage form.

9. The antibiotic composition of claim 8 wherein the composition includes the dosage of antibiotic for a twenty-four hour period.

10. The antibiotic composition of claim 9 wherein the first dosage form includes from 30% to 80% of the antibiotic delivered by the composition and the remainder of the antibiotic is delivered by the third dosage form.

11. A process for treating a patient for a bacterial infection comprising treating the patient by administration of the antibiotic composition of claim 1.

12. A process for treating a patient for a bacterial infection comprising treating the patient by administration of the antibiotic composition of claim 2.

13. A process for treating a patient for a bacterial infection comprising treating the patient by administration of the antibiotic composition of claim 3.

14. A process for treating a patient for a bacterial infection comprising treating the patient by administration of the antibiotic composition of claim 4.

15. A process for treating a patient for a bacterial infection comprising treating the patient by administration of the antibiotic composition of claim 5.

16. A process for treating a patient for a bacterial infection comprising treating the patient by administration of the antibiotic composition of claim 6.

17. A process for treating a patient for a bacterial infection comprising treating the patient by administration of the antibiotic composition of claim 7.

18. A process for treating a patient for a bacterial infection comprising treating the patient by administration of the antibiotic composition of claim 8.

19. A process for treating a patient for a bacterial infection comprising treating the patient by administration of the antibiotic composition of claim 9.

20. A process for treating a patient for a bacterial infection comprising treating the patient by administration of the antibiotic composition of claim 10.

21. The antibiotic composition of claim 1, wherein the inhibitor released from the fourth dosage form reaches a maximum serum concentration in no more than 12 hours.

22. The antibiotic composition of claim 1, wherein the the inhibitor released from the second dosage form reaches a maximum serum concentration after the antibiotic released from the first dosage form reaches a maximum serum concentration; the antibiotic released from the third dosage form reaches a maximum serum concentration after the inhibitor released from the second dosage form reaches a maximum serum concentration; and the inhibitor released from the fourth dosage form reaches a maximum serum concentration after the antibiotic released from the third dosage form reaches a maximum serum concentration.

23. The antibiotic composition of claim 1, wherein the antibiotic released from the first dosage form reaches a maximum serum concentration in no more than about three hours after administration; wherein the inhibitor released from the second dosage form reaches a maximum serum concentration in about three to six hours after administration and after the first dosage form reaches a maximum serum concentration; wherein the antibiotic released from the third dosage form reaches a maximum serum concentration in from about six to nine hours after administration and after the second dosage from reaches a maximum serum concentration; and wherein the inhibitor released from the fourth dosage form reaches a maximum serum concentration in no more than twelve hours after administration and after the third dosage form reaches a maximum serum concentration.

24. A once-a-day antibiotic product comprising: first, second, third, and fourth dosage forms, wherein said first dosage form includes at least one antibiotic with a beta-lactam ring or portion thereof and a pharmaceutically acceptable carrier; said second dosage form includes at least one beta-lactamase inhibitor and a pharmaceutically acceptable carrier; said third dosage form includes at least a one antibiotic with a beta-lactam ring or portion thereof and a pharmaceutically acceptable carrier; said fourth dosage form includes at least one beta-lactamase inhibitor and a pharmaceutically acceptable carrier; said first dosage form is an immediate release dosage form; said second, third, and fourth dosage forms are delayed release dosage forms; said first dosage form and said second dosage form having release profiles whereby the maximum serum concentration of the inhibitor released from the second dosage form is reached at a time after the maximum serum concentration is reached for the antibiotic released from the first dosage form, the third dosage form having a release profile such that maximum serum concentration of the antibiotic released from the third dosage form is reached at a time after the time at which the maximum serum concentration for the inhibitor released from the second dosage form is achieved, and the fourth dosage form having a release profile whereby the inhibitor released from the fourth dosage form achieves a maximum serum concentration at a time that is after the time at which the maximum serum concentration of the antibiotic released from the third dosage form is achieved; wherein there is successive alternate release of antibiotic and inhibitor and Cmax for the fourth dosage form is reached in no more than about 12 hours; and said once-a-day antibiotic product contains the total dosage of antibiotic for a twenty-four hour period.

25. The antibiotic composition of claim 24 wherein the second dosage form initiates release of inhibitor at least one hour after initiation of release of antibiotic from the first dosage form, the third dosage form initiates release of antibiotic at least one hour after initiation of release of inhibitor from the second dosage form and the fourth dosage form initiates release of inhibitor at least one hour after initiation of release of antibiotic from the third dosage form.

26. The antibiotic composition of claim 24 wherein the inhibitor is released from the second dosage form after the antibiotic released from the first dosage form reaches maximum serum concentration; the antibiotic is released from the third dosage form after the inhibitor released from the second dosage form reaches maximum serum concentration; and the inhibitor is released from the fourth dosage form after antibiotic released from the third dosage form reaches maximum serum concentration.

27. The antibiotic composition of claim 24, wherein the the inhibitor released from the second dosage form reaches a maximum serum concentration after the antibiotic released from the first dosage form reaches a maximum serum concentration; the antibiotic released from the third dosage form reaches a maximum serum concentration after the inhibitor released from the second dosage form reaches a maximum serum concentration; and the inhibitor released from the fourth dosage form reaches a maximum serum concentration after the antibiotic released from the third dosage form reaches a maximum serum concentration.

28. The antibiotic composition of claim 24, wherein the antibiotic released from the first dosage form reaches a maximum serum concentration in no more than about three hours after administration; wherein the inhibitor released from the second dosage form reaches a maximum serum concentration in about three to six hours after administration and after the first dosage form reaches a maximum serum concentration; wherein the antibiotic released from the third dosage form reaches a maximum serum concentration in from about six to nine hours after administration and after the second dosage form reaches a maximum serum concentration; and wherein the inhibitor released from the fourth dosage form reaches a maximum serum concentration in no more than twelve hours after administration and after the third dosage form reaches a maximum serum concentration.

29. A process for treating a patient for a bacterial infection comprising treating the patient by administration of the antibiotic composition of claim 21.

30. A process for treating a patient for a bacterial infection comprising treating the patient by administration of the antibiotic composition of claim 22.

31. A process for treating a patient for a bacterial infection comprising treating the patient by administration of the antibiotic composition of claim 23.

32. A process for treating a patient for a bacterial infection comprising treating the patient by administration of the antibiotic composition of claim 24.

33. A process for treating a patient for a bacterial infection comprising treating the patient by administration of the antibiotic composition of claim 25.

34. A process for treating a patient for a bacterial infection comprising treating the patient by administration of the antibiotic composition of claim 26.

35. A process for treating a patient for a bacterial infection comprising treating the patient by administration of the antibiotic composition of claim 27.

36. A process for treating a patient for a bacterial infection comprising treating the patient by administration of the antibiotic composition of claim 28.

* * * * *

UNITED STATES PATENT AND TRADEMARK OFFICE
CERTIFICATE OF CORRECTION

PATENT NO. : 6,565,882 B2
DATED : May 20, 2003
INVENTOR(S) : Edward M. Rudnic

It is certified that error appears in the above-identified patent and that said Letters Patent is hereby corrected as shown below:

Title page,
Below item "[75]", insert -- [73] Assignee: Advancis Pharmaceutical Corp., Gaithersburg MD (US) --

Below "*Assistant Examiner*--Amy E. Pulliam", insert
-- [74] *Attorney, Agent, or Firm*--Elliot M. Olstein; Raymond E. Stauffer --

Column 11,
Line 28, change "from" to -- form --

Signed and Sealed this

Sixteenth Day of September, 2003

JAMES E. ROGAN
*Director of the United States Patent and Trademark Office*